US008958071B2

(12) United States Patent
Margalit et al.

(10) Patent No.: US 8,958,071 B2
(45) Date of Patent: Feb. 17, 2015

(54) INTEGRATED OPTICAL SENSOR

(75) Inventors: Mordehai Margalit, Yaaqov (IL); Ariel Lipson, Tel Aviv (IL)

(73) Assignee: Empire Technology Development LLC, Wilmington, DE (US)

(*) Notice: Subject to any disclaimer, the term of this patent is extended or adjusted under 35 U.S.C. 154(b) by 297 days.

(21) Appl. No.: 13/509,699

(22) PCT Filed: Nov. 15, 2011

(86) PCT No.: PCT/US2011/060724
§ 371 (c)(1),
(2), (4) Date: May 14, 2012

(87) PCT Pub. No.: WO2013/074084
PCT Pub. Date: May 23, 2013

(65) Prior Publication Data
US 2013/0122537 A1    May 16, 2013

(51) Int. Cl.
*G01N 21/00* (2006.01)
*G01N 21/31* (2006.01)
*G01N 21/65* (2006.01)

(52) U.S. Cl.
CPC .............. *G01N 21/31* (2013.01); *G01N 21/65* (2013.01)
USPC ......................................................... 356/432

(58) Field of Classification Search
CPC .............. G01N 21/65; G01N 21/0303; G01N 33/1893; G01N 2021/651; G01N 2021/1751; G01N 15/1436; G01N 21/314; G01N 21/39
USPC .................. 356/432–444, 244–246
See application file for complete search history.

(56) References Cited

U.S. PATENT DOCUMENTS

| 3,489,906 | A | * | 1/1970 | Beer .............................. 250/575 |
| 3,790,289 | A | * | 2/1974 | Schmidt ........................ 356/434 |
| 4,491,730 | A | * | 1/1985 | Pedersen ...................... 250/343 |
| 4,578,762 | A | * | 3/1986 | Wong ............................ 702/32 |
| 4,650,329 | A | * | 3/1987 | Barrett et al. ................. 356/481 |
| 5,159,601 | A | * | 10/1992 | Huber ............................ 372/6 |
| 5,262,644 | A | * | 11/1993 | Maguire ................. 250/339.08 |
| 5,280,786 | A | | 1/1994 | Wlodarczyk et al. |
| 5,387,971 | A | * | 2/1995 | Koashi et al. ................. 356/246 |
| 5,412,465 | A | * | 5/1995 | Baylor et al. ................. 356/301 |

(Continued)

FOREIGN PATENT DOCUMENTS

| AU | 2002347372 A1 | 6/2003 |
| AU | 2002347379 A1 | 7/2003 |

(Continued)

OTHER PUBLICATIONS

International Search Report and Written Opinion for PCT/US2011/060724 dated Feb. 9, 2012.

(Continued)

*Primary Examiner* — Michael A Lyons
*Assistant Examiner* — Shawn Decenzo
(74) *Attorney, Agent, or Firm* — Pepper Hamilton LLP

(57) ABSTRACT

Optical sensors for use in examining and analyzing a fluid material are described. The optical sensors include a channel configured to transport a fluid material to be examined and analyzed, a first waveguide positioned adjacent to the channel and configured to guide radiation through the channel and a first tunable grating defined on the first waveguide and configured to variably define a cavity for selecting a first wavelength of the radiation.

26 Claims, 6 Drawing Sheets

(56) References Cited

U.S. PATENT DOCUMENTS

| | | | |
|---|---|---|---|
| 5,444,528 A * | 8/1995 | Puschell | 356/73 |
| 5,862,273 A * | 1/1999 | Pelletier | 385/12 |
| 6,020,207 A * | 2/2000 | Liu | 436/164 |
| 6,103,535 A * | 8/2000 | Pilevar et al. | 436/518 |
| 6,342,948 B1 * | 1/2002 | Gilby | 356/436 |
| 6,429,022 B1 | 8/2002 | Kunz et al. | |
| 6,834,237 B2 * | 12/2004 | Noergaard et al. | 702/19 |
| 6,961,599 B2 * | 11/2005 | Lambert et al. | 600/318 |
| 7,068,897 B2 * | 6/2006 | Russell et al. | 385/123 |
| 7,212,693 B2 | 5/2007 | Carr et al. | |
| 7,245,379 B2 | 7/2007 | Schwabe | |
| 7,477,384 B2 | 1/2009 | Schwabe | |
| 7,564,548 B2 * | 7/2009 | Flanders et al. | 356/301 |
| 8,538,207 B2 * | 9/2013 | Gates et al. | 385/14 |
| 2004/0038251 A1 * | 2/2004 | Smalley et al. | 435/6 |
| 2004/0124366 A1 * | 7/2004 | Zeng et al. | 250/458.1 |
| 2005/0068536 A1 | 3/2005 | Schwabe | |
| 2005/0094918 A1 | 5/2005 | Gunn, III | |
| 2005/0135723 A1 | 6/2005 | Carr et al. | |
| 2006/0045145 A1 * | 3/2006 | Arahira | 372/18 |
| 2006/0176478 A1 * | 8/2006 | Clarke et al. | 356/301 |
| 2007/0268489 A1 | 11/2007 | Schwabe | |
| 2009/0194707 A1 | 8/2009 | Tjin et al. | |
| 2010/0079756 A1 | 4/2010 | Schwabe | |
| 2011/0216319 A1 | 9/2011 | Schwabe | |

FOREIGN PATENT DOCUMENTS

| | | |
|---|---|---|
| AU | 2006339611 A1 | 9/2007 |
| EP | 0576670 A1 | 1/1994 |
| EP | 1455747 A1 | 9/2004 |
| EP | 1548424 A2 | 6/2005 |
| EP | 1710564 A2 | 10/2006 |
| EP | 2002240 A1 | 12/2008 |
| EP | 1454123 B1 | 3/2010 |
| GB | 2383127 B | 6/2003 |
| JP | 2005513476 A | 5/2005 |
| JP | 2005181334 A | 7/2005 |
| JP | 2009529137 A | 8/2009 |
| KR | 20050063699 A | 6/2005 |
| WO | WO 93/13707 A1 | 7/1993 |
| WO | WO 03/051325 A1 | 6/2003 |
| WO | WO 03/054525 A2 | 7/2003 |
| WO | WO2007/102783 A1 | 9/2007 |

OTHER PUBLICATIONS

Bog et al., High-Q microfluidic cavities in silicon-based two-dimensional photonic crystal structures, Optics Letters (Oct. 1, 2008), 33(19):2206-2208.

Domachuk et al., Compact resonant integrated microfluidic refractometer, Applied Physics Letters (Nov. 7, 2005), 88:093513-1-093513-3.

Levy et al., On-chip microfluidic tuning of an optical microring resonator, Applied Physics Letters (Nov. 16, 2005), 88:111107-1-111107-3.

Nunes et al., Photonic crystal resonator integrated in a microfluidic system, Department of Micro- and Nanotechnology, Technical University of Denmark, DTU, Denmark, pp. 1-13, http://arxiv.org/ftp/arxiv/papers/0808/0809.3865.pdf, (printed from internet Feb. 29, 2012).

Psaltis et al., Developing optofluidic technology through the fusion of microfluidics and optics, Nature (Jul. 27, 2006), 442:381-386.

Hu, J. et al., Planar waveguide-coupled, high-index-contrast, high-Q resonators in chalcogenide glass for sensing, *Optics Letters*, (Dec. 2008), 33(21), pp. 1-12.

* cited by examiner

INTEGRATED OPTICAL SENSOR

CLAIM OF PRIORITY

This application is a national phase application under 35 U.S.C. §371 of International Application No. PCT/US2011/060724, filed Nov. 15, 2011, which is incorporated herein by reference in its entirety.

BACKGROUND

Testing for and identifying materials in fluid media is becoming increasingly important in various fields such as medical and pharmaceutical research and development, food preparation, environmental studies, and other similar fields. Typically, these fields require the detection of materials such as contaminants, pollutants or other foreign objects in a fluid such as a gas or liquid.

One common type of detection device is an optical sensor. Light is a useful tool in identifying materials in a liquid or gas. Typically, light is emitted at a particular wavelength and directed through the liquid or gas to a detector where the light is collected. Materials in the liquid or gas can cause a disturbance or change to the wavelength or other measurable characteristics of the emitted light. Methods such as Raman scattering analysis (i.e., analyzing scattering patterns of protons), absorption analysis, fluorescence analysis, plasmon analysis (i.e., analysis of plasma oscillation), and Fourier transform infrared spectroscopy (FTIR) are commonly used to determine or identify any materials in the liquid or gas.

In most applications, a detection device is precisely configured to detect materials at very low concentrations. Detection devices incorporating optical sensors have been proven to reach the desirable detection levels. However, it is a challenge to produce an integrated, low-cost optical sensor capable of reaching the desired detection levels. Often, the creation, delivery and detection of light require large apparatuses which are not amenable to size or cost reduction.

SUMMARY

In one general respect, the embodiments disclose an optical sensor including a channel configured to transport a fluid material to be examined, a first waveguide positioned adjacent to the channel and configured to guide radiation through the channel and a first tunable grating defined on the first waveguide and configured to variably adjust a wavelength of the radiation.

In another general respect, the embodiments disclose an optical sensor assembly including a radiation source, a sensor, and at least one optical sensor positioned between the radiation source and the sensor. The at least one optical sensor includes a channel configured to transport a fluid material to be examined, a first waveguide positioned adjacent to the channel and configured to guide radiation through the channel, and a first tunable grating defined on the first waveguide and configured to variably define a cavity for selecting a first wavelength of the radiation.

In another general respect, the embodiments disclose an optical sensor including a first channel configured to transport a fluid material to be examined, a first waveguide positioned adjacent to the first channel and configured to guide radiation through the first channel, a first tunable grating defined on the first waveguide and configured to variably define a cavity for selecting a first wavelength of the radiation, and a reference channel positioned adjacent to the first channel such that the radiation passing through the first channel passes through the reference channel.

In another general respect, the embodiments disclose a method of analyzing a fluid material. The method includes providing an optical sensor, the optical sensor including a channel configured to transport a fluid material, a first waveguide positioned adjacent to the channel and configured to guide radiation through the channel, and a first tunable grating defined on the first waveguide and configured to variably define a cavity for selecting a first wavelength of the radiation. The method further includes providing a fluid material to be tested, transporting the fluid material through the channel past the first waveguide, and analyzing the fluid material based upon radiation passed through the fluid material.

In another general respect, the embodiments disclose a kit including an optical sensor and instructions for operating the optical sensor. The optical sensor includes a channel configured to transport a fluid material, a first waveguide positioned adjacent to the channel and configured to guide radiation through the channel, and a first tunable grating defined on the first waveguide and configured to variably define a cavity for selecting a first wavelength of the radiation.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

As used herein, an "optical waveguide" or "waveguide" refers to a physical structure that guides electromagnetic waves in the optical spectrum. Common examples of waveguides include optical fiber waveguides and rectangular waveguides.

A "diffraction grating" or "grating" refers to an optical component with a periodic structure configured to split and diffract light into several beams traveling in different intensities and directions based upon the wavelength of the light. A "tunable grating" refers to a grating having an adjustable grating phase such that a resonance of the grating may be changed.

A "fluid" refers to a state of matter that deforms or flows as a result of applied shear stress. Examples of fluids include, but are not limited to, liquids, gases, plasmas, viscoelastic fluids and other states of matter having similar physical properties.

Figure 1A:
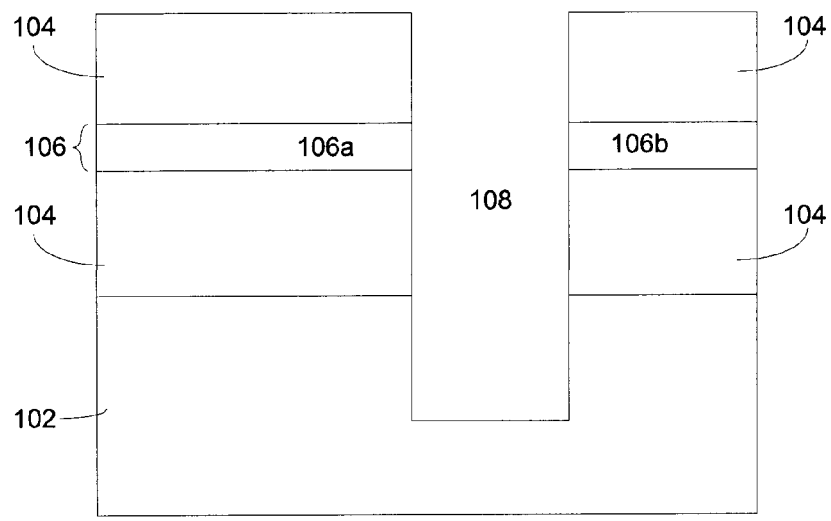
FIGS. 1A and 1B illustrate an exemplary optical sensor.
Figure 1B:
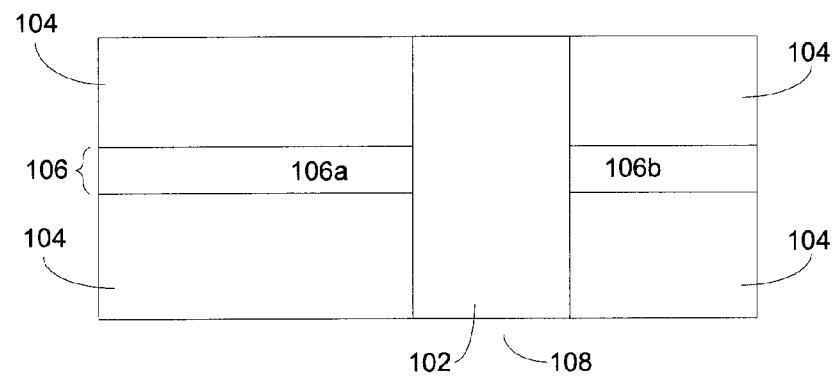

FIGS. 1A and 1B illustrate a side-view (FIG. 1A) and a top view (FIG. 1B) of an exemplary optical sensor 100. The sensor 100 may include several layers built upon a silicon substrate 102. An exemplary silicon substrate 102 may sized in the range of 500 um to 2000 um. Various glass layers 104 may be stacked on, applied to or otherwise adhered to the silicon substrate 102. An exemplary glass layer 104 may be sized in the range of 0.1 um to 500 um. A waveguide 106 may be placed between two of the glass layers. Alternatively, one or more cladding layers may surround the waveguide 106 such that the waveguide propagates light in a guided fashion toward a channel 108. An exemplary waveguide 106 may be sized in the range of 0.1 um to 10 um.

The trench or channel 108 may be positioned within the glass layers 104 and waveguide 106 such that the channel bifurcates the waveguide into a first waveguide 106a and a second waveguide 106b. Light may be guided via the first waveguide 106a though the channel 108 to the second waveguide 106b. The channel 108 may be created by etching the silicon substrate 102, the glass layers 104 and the waveguide 106 to create the channel. An exemplary channel 108 may be about 100 microns wide and about 50 to 100 microns deep. The width of the channel 108 may be accurately controlled such that there is low optical loss as light passes through the channel. The channel 108 may also include a chemical adhesion layer to capture a portion of the fluid to be analyzed, thereby exposing the fluid to the light for an extended period of time, increasing sensitivity of the sensor. An exemplary chemical adhesion layer is a compact polymer layer having a binding capacity of approximately one or several protein monolayers. An immobilization layer may be further applied to capture biotinylated molecules. It should be noted these chemical adhesion layers are shown by way of example only and other chemical adhesion layers may be added based upon the fluid being passed through the channel.

In order to propagate high quality light through the channel 108, one or more reflective structures may be created within the waveguide. The reflective structures may be both highly reflective (e.g., >99% reflective) and capable of directing a broad band of light to support a tunable range of a light source. For example, if a tunable laser is used as the light source, the waveguide 106 may be rated to handle a tunable light range of the laser. One approach to creating the reflective structures in the waveguides is to create a periodic reflective structure. This structure may be created by UV patterning in a glass waveguide; masking, lithographing and etching either partially or throughout the waveguide; selectively applying an overlay material; and deep reactive ion etching.

Figure 2A:
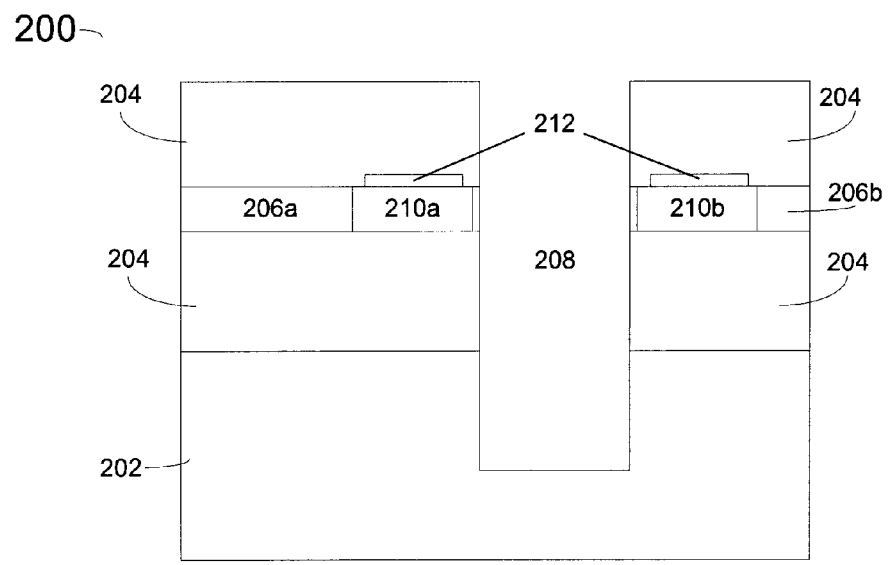
FIGS. 2A and 2B illustrate an alternative exemplary optical sensor.
Figure 2B:
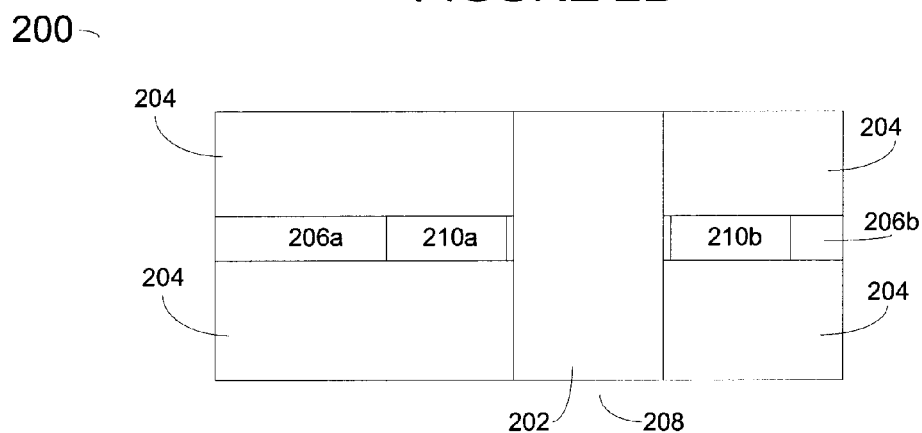

As arranged in FIGS. 1A and 1B, the sensor 100 provides a one-dimensional directing structure for light and a fluid channel (via the channel 108) for transporting a fluid past the waveguide 106 such that light emitted by the waveguide interacts with the fluid. FIGS. 2A and 2B illustrate a second sensor 200 incorporating tunable gratings 210a and 210b such that the resonance of the gratings may be changed, thereby altering a wavelength of the light being directed through the fluid.

Similarly to FIGS. 1A and 1B, FIGS. 2A and 2B illustrate a side-view (FIG. 2A) and a top view (FIG. 2B) of the optical sensor 200. The sensor 200 may include several layers built upon a silicon substrate 202 through which a channel 208 passes, bifurcating the layers. Various glass layers 204 may be stacked on, applied to or otherwise adhered to the silicon substrate 202. Waveguides 206a and 206b may be placed on either side of the channel 208 between two of the glass layers 204. Alternatively, one or more cladding layers may surround the waveguides 206a and 206b such that the waveguides propagate light in a guided fashion toward the channel 208.

Tunable gratings 210a and 210b may be placed within waveguides 206a and 206b, respectively. The gratings 210a and 210b may be tunable such that a resonance of the gratings may be changed by altering a defined cavity space within the gratings, thereby altering a wavelength of the light passing through each of the waveguides 206a and 206b. By positioning the gratings 210a and 210b on each side of the channel, sensor 200 provides a one-dimensional resonant structure for directing light through the channel 208, and the channel provides a fluid channel for transporting a fluid such that the light interacts with the fluid as the fluid passes through the sensor. The gratings 210a and 210b may also select a preferred wavelength of the light for interaction with the fluid. If the light source is configured to provide a wide range of wavelengths, the wavelength that matches the setting of grating 210a or 210b may be greatly enhanced. The waveguides 206a and 206b may act to limit the light to a single plane, thereby further increasing the amount of light propagated through the channel 208.

To enable tuning of the gratings 210a and 210b, at least one tuning element 212 may be positioned adjacent to each grating. The tuning elements 212 may be configured to alter the resonance of the gratings 210a and 210b such that the wavelength of the light passing through the gratings is altered. For example, the tuning elements 212 may be a thin film resistor applied to each of the gratings 210a and 210b. An electrical current may be applied to each of the thin film resistors, thereby heating each of the gratings 210a and 210b, causing a change in the resonance of the gratings as a result of the thermoelectric effect of thin film resistors. Alternative tuning elements 212 may include, for example, mechanical tuning devices (such as a microelectromechanical system (MEMS)), optical and electrical tuning elements, and thermal tuning elements.

Depending on the intended application of the sensor 200, each of the gratings 210a and 210b may be adjusted such that they have the same resonance or, conversely, a unique resonance. To achieve the same resonance, a single current is sent to a thin film resistor 212 adjacent to each of the gratings 210a and 210b. The single current heats the gratings 210a and 210b uniformly, thereby resulting in the same adjusted resonance for each grating. To achieve unique resonances, a first current may be applied to a first thin film resistor tuning element 212 adjacent to the grating 210a. The first current may cause the first thin film resistor tuning element 212 to heat the grating 210a to a specific temperature, thereby altering the resonance of the grating 210a to a first value. Alternatively or additionally, a second current may be applied to a second thin film resistor tuning element 212 adjacent to the grating 210b. The second current may cause the second thin film resistor tuning element 212 to heat the grating 210b to a second temperature, thereby altering the resonance of the grating 210b to a second value unique from the first value. For example, depending on the surface area and construction material, an exemplary thin film resistor 212 may receive between 10 and 200 mW of power, thereby increasing the temperature of the thin film resistor approximately 100° C. For a tunable grating manufactured from silicon dioxide, this temperature change may result in 4 nm of tuning capabilities. For a tunable grating manufactured from silicon or polymers having similar thermal characteristics, this temperature change may result in 40 nm of tuning capabilities.

The sensor 200 may optionally incorporate at least one cooling component for maintaining a temperature of a fluid being passed through the channel 208. For example, when using heating to adjust the resonance of the gratings 210a and 210b, the temperature of the glass layers 204 and the silicon substrate 202 may increase accordingly. A cooling element may maintain the fluid at a low temperature prior to the fluid passing through the channel 208 such that an increase in temperature of the fluid does not result in incorrect analysis of the fluid.

Figure 3:
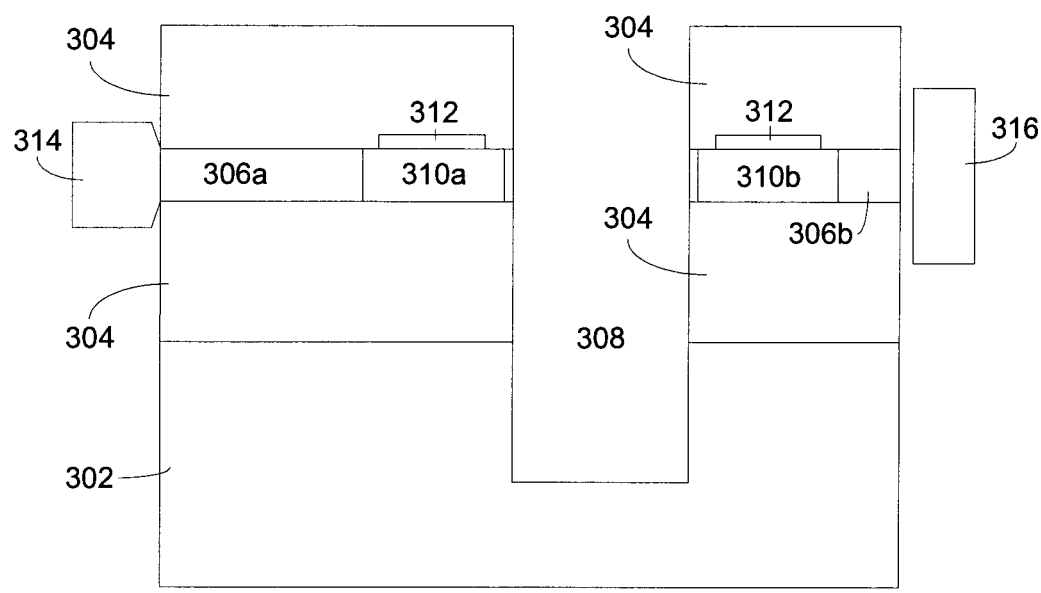
FIG. 3 illustrates an exemplary optical sensor assembly.

FIG. 3 illustrates an exemplary sensor assembly 300 including a similar optical sensor to sensor 200 as described above. The assembly 300 may include several layers built upon a silicon substrate 302 through which a channel 308 passes, bifurcating the layers. Various glass layers 304 may be stacked on, applied to or otherwise adhered to the silicon substrate 302. Waveguides 306a and 306b may be placed on either side of the channel 308 between two of the glass layers 304. Alternatively, one or more cladding layers may surround the waveguides 306a and 306b such that the waveguides propagate light in a guided fashion toward the channel 308.

Tunable gratings 310a and 310b may be placed within waveguides 306a and 306b, respectively. The gratings 310a and 310b may be tunable such that a resonance of the gratings may be changed, thereby altering a selection of an enhanced wavelength of the light passing through each of the waveguides 306a and 306b. To enable tuning of the gratings 310a and 310b, a tuning element 312 may be positioned adjacent to each grating. The tuning elements 312 may be configured to alter the resonance of the gratings 310a and 310b such that the wavelength of the light passing through the gratings is altered.

The assembly 300 may optionally include at least one radiation or light source 314. The light source 314 may be a laser positioned adjacent to the optic sensor, specifically adjacent to the waveguide 306a such that any light emitted by the light source is directed through the waveguide, through grating 310a (where the selection of an enhanced wavelength of the light may be altered depending on the resonance of the grating) and through the channel 308 and any fluid contained therein. After passing through the fluid, the light may pass through grating 310b (where, again, the selection of an enhanced wavelength of the light may be altered depending on the resonance of the grating), through the waveguide 306b to a radiation or light sensor 316. The light sensor 316 may be operably connected to a computer or other processing device where information related to the light as received at the light sensor is further analyzed to identify any potential foreign materials in the fluid.

The assembly 300 may further include at least one polished facet adjacent to the waveguide 306a such that the waveguide reaches the outer edge as defined by the glass layers 304 and directly contacts the light source 314, eliminating any potential interference to transmitted light before the light enters the waveguide. The facet may be further configured to receive an optical fiber from a light source such as a laser, positioning the fiber such that a core of the fiber is concentric with the waveguide 306a. Thus, light can travel in a linear and planar path from the light source 314, through the channel 308 and to the sensor 316.

Figure 4:
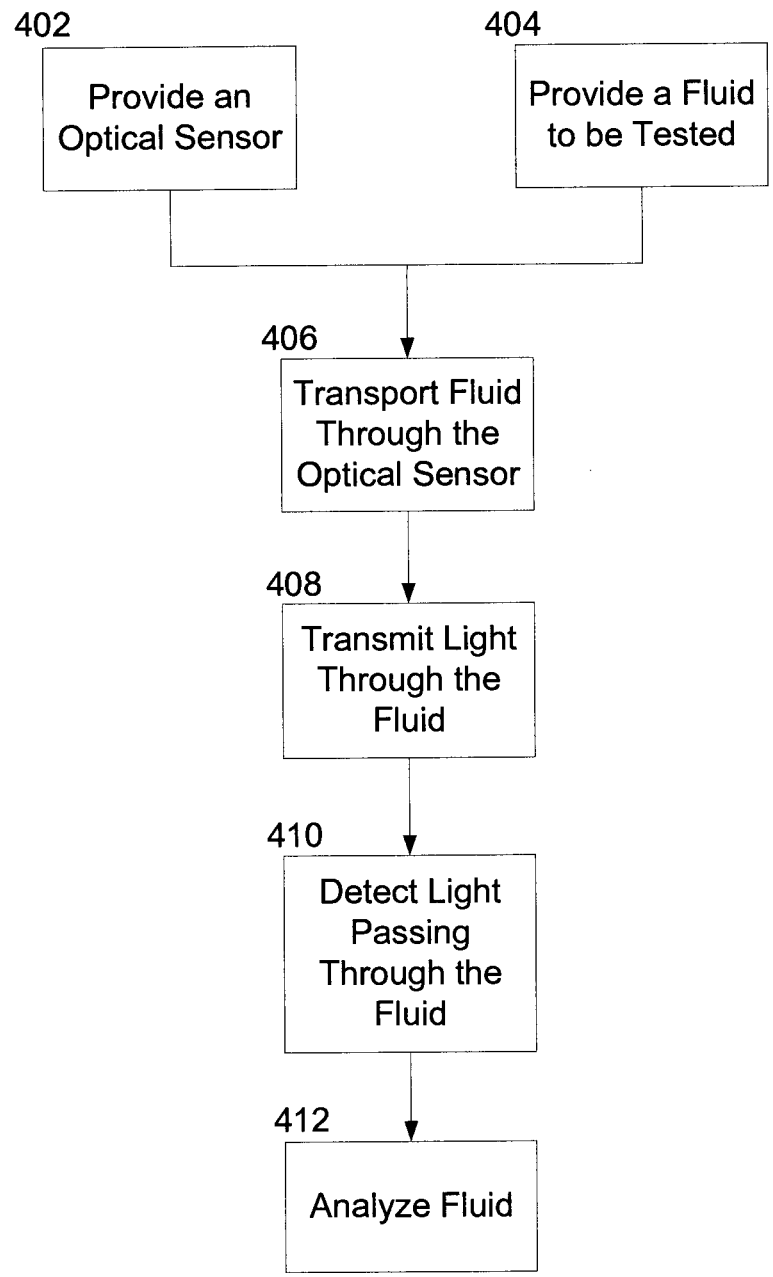
FIG. 4 illustrates an exemplary method of analyzing a fluid.

FIG. 4 illustrates an exemplary method for analyzing a fluid material using an exemplary sensor assembly, such as sensor assembly 300. It should be noted that while components related to sensor assembly 300 are discussed in regard to FIG. 4, the method as shown in FIG. 4 is not limited to sensor assembly 300.

A user wishing to analyze a fluid using the principles described herein may provide 402 an optical sensor or sensor assembly, such as sensor assembly 300. The user may also provide 404 a fluid to be tested. For example, the user may test a quantity of water to determine if there are any undesired contaminants in the water. The fluid to be tested may be transported 406 through the sensor assembly 300. The light source 314 may transmit 408 light that passes through waveguide 306a and grating 310a and into the channel 308 and the sample of the fluid. Depending on the type of testing and analysis the user is doing, the grating 310a may be adjusted accordingly such that the wavelength of the light transmitted 408 through the fluid is properly controlled. After the light passes through the fluid, the light passes through grating 310b (which may be adjusted similar to grating 310a) and the waveguide 306b. The light passed through the fluid may then be detected 410 at the light sensor 316.

The light sensor 316 may be operably connected to at least one processing device such that information related to the detected light is passed to the processing device and further analyzed 412. Based upon the analysis 412, any contamination or other quality related issues related to the fluid may be determined. Depending on the configuration of the light sensor 316 and the processing device, various types of analysis 412 may be performed. For example, a Raman scattering analysis, white light spectroscopy, or absorption analysis may be performed. Depending on the analysis used, the gratings 310a and 310b may be tuned accordingly. For example, if Raman scattering analysis is used, the gratings 310a and 310b may be configured to scan a small range of wavelengths during the test, thereby increasing the sensitivity of the sensor. For example, if the light source in a Raman scattering analysis is configured to produce green light at 532 nm, resulting Raman shift information may be between 542-588 nm or, depending on the material used to manufacture the gratings 310a and 310b, between 546-633 nm.

Figure 5A:
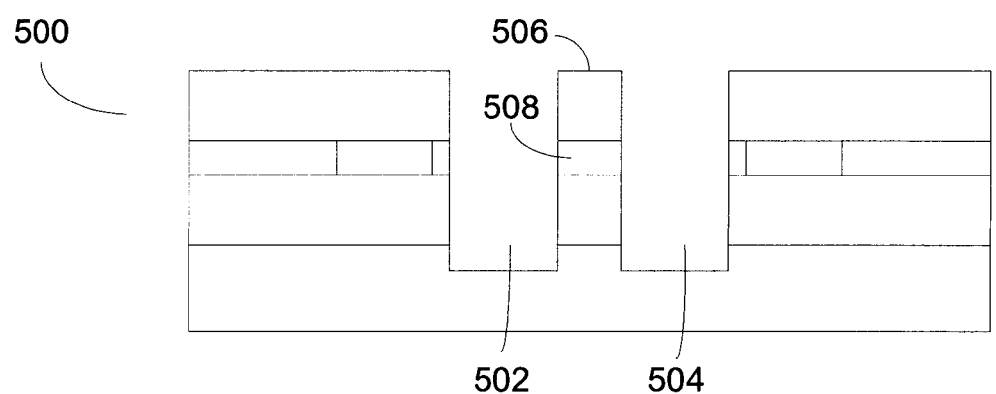
FIGS. 5A, 5B and 5C illustrate alternative optical sensors.
Figure 5B:
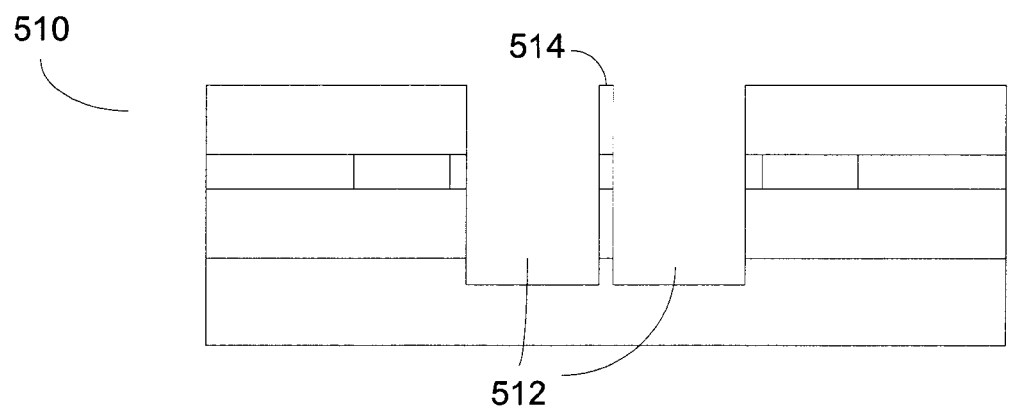

The method and sensors as described above may be augmented to include multiple fluid cavities and additional tunable gratings. As shown in FIG. 5A, a sensor 500 may include two sequential cavities 502 and 504 be placed adjacent to each other, with a wall 506 separating the two cavities. The wall may include an additional tunable grating 508 such that light passing through the second channel 504 has a unique wavelength as compared to light passing through the first channel 502. Alternatively, FIG. 5B illustrates a sensor 510 having a large channel 512 including a thin wall 514 for separating two fluids as the fluids pass though the channel. The exemplary sensors 500 and 510 as shown in FIGS. 5A and 5B may be used to provide a reference channel when testing a fluid. For example, a reference fluid may be passed through a first channel (or pathway through the channel as in FIG. 5B) while a second fluid is passed through a second channel (or pathway through the channel as in FIG. 5B). By using a differential measurement related to the reference channel, a processing and analyzing device may remove any system and material noise or interference at the sensor level, thereby providing a calibrated sensor for determining any foreign materials. Additionally, the exemplary sensors 500 and 510 may provide parallel testing of different fluids simultaneously using the same sensor, thereby increasing throughput of a single sensor.

Figure 5C:
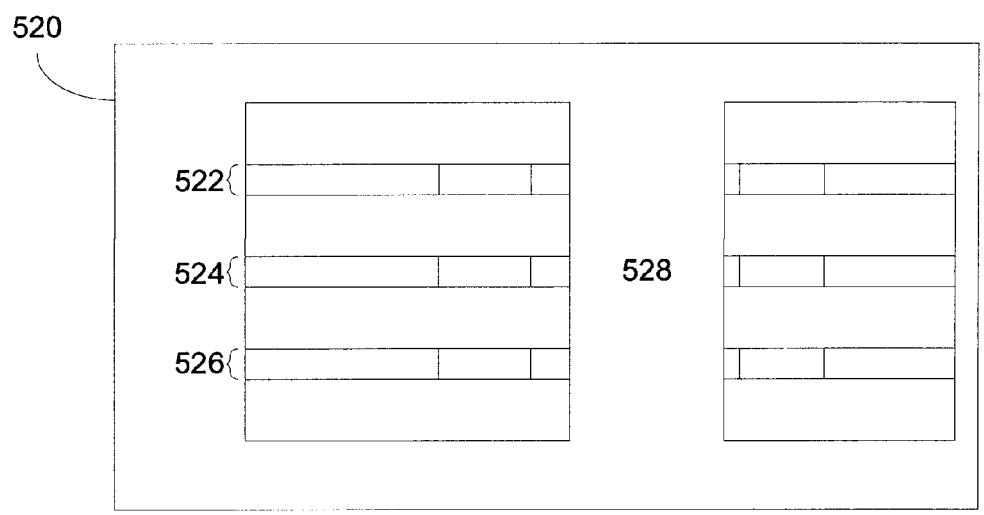

FIG. 5C illustrates yet another exemplary sensor 520. In this example, multiple waveguide/grating sets 522, 524 and 526 are shown about a single channel 528. With this arrangement, each waveguide/grating set may share a single light source while having a unique resonance. Thus, multiple wavelengths of light may be passed through a fluid in the channel 528 simultaneously, thereby providing for parallel testing of different optical analysis methods. Similarly, the detected light from each of the waveguide/grating sets 522, 524 and 526 may be analyzed using a different analysis method. For example, waveguide/grating set 522 may be used to scan a range of frequencies for a Raman scattering analysis, waveguide/grating set 524 may be set to a specific wavelength or range of wavelengths for white light spectroscopy, and waveguide/grating set 526 may be set to a specific wavelength or range of wavelengths for absorption analysis.

EXAMPLE 1

Kit for Consumer Use

A kit may be sold to consumers for testing the quality of and any foreign contamination in a fluid. The kit may include an optical sensor similar to those discussed above (e.g., sensor 200). The optical sensor may be modified so that a silicon substrate is mountable on a circuit board via a standard manufacturing process such as VLSI (very-large-scale integration). Processing components configured to analyze a fluid sample may also be mounted on the circuit board and operably connected to a light source and light sensor placed about the optical sensor on the circuit board. The circuit board may be enclosed in a case, the case including an aperture for inserting a sample of a fluid to be tested, a user interface for initializing a test, and a display for indicating results of the test. The kit may also include instructions defining a standard operating procedure for the optical sensor as well as a listing of how to interpret any displayed results. Specific consumers may include homeowners testing the quality of the water in their homes, pool owners testing chemical levels of pool water, mechanics or garage owners testing the quality of various fluids associated with motor use and maintenance (e.g., engine oil, coolant, transmission fluid), and other similar consumers testing fluid quality.

EXAMPLE 2

Testing of Medications During Manufacture

A pharmaceutical company may design an assembly line such that at various points along the assembly line sensor assemblies are positioned to test the quality of fluids being used to manufacture liquid medications. The optical sensors as described above (e.g., sensor assembly 300) may be modified to include a valve assembly such that, at specific times, a quantity of fluid may be redirected from the assembly line into a sensor assembly. The fluid may be tested for quality and any foreign contaminants. Control processors for the assembly line may be in communication with the sensor assemblies such that if any foreign contaminants are detected, the manufacturing is halted until the source of the contaminants is discovered and all compromised areas of the assembly line are cleaned.

EXAMPLE 3

Testing Water Quality During Decontamination

A utility company such as a water and sewage decontamination facility may incorporate sensor assemblies such that at various points throughout the decontamination process to test the water quality at various stages. The optical sensors as described above (e.g., sensor assembly 300) may be modified to include a valve assembly such that, at specific times, a quantity of water may be redirected from the decontamination process into an optical sensor assembly. The water may be tested for quality and foreign contaminant levels. The quality and contaminant levels may be compared to acceptable levels for that stage of decontamination, and the decontamination process may be adjusted accordingly.

More specifically, a water treatment facility may want to test water for various water-borne organisms such as protozoa of the genus *Cryptosporidium* and protozoa of the genus *Giardia*. The water treatment facility may incorporate a Raman spectroscopy analysis system incorporating one or more of the optical sensors as described above. The analysis system may include a laser or other light source configured to irradiate water as the water passes through one or more of the optical sensors. The laser may be configured to produce light ranging from approximately 125 nm to approximately 800 nm, resulting in discontinuous Raman spectra ranging from approximately 60 to 410 nm and from approximately 612 to 800 nm. However, based upon the specific elements the water treatment facility may want to detect, specific wavelengths may be enhanced by the tunable gratings in the optical sensors, thereby producing narrow Raman spectra relating to those specific wavelengths for more thorough analysis and possible pathogen detection.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. An optical sensor comprising:
    a channel configured to transport a fluid material to be examined;
    a first waveguide positioned adjacent to the channel and configured to guide radiation through the channel;
    a first tunable grating defined on the first waveguide and configured to variably define a first cavity for selecting a first wavelength of the radiation for the first waveguide;
    a second waveguide positioned adjacent to the channel;
    a second tunable grating defined on the second waveguide and configured to variably define a second cavity for selecting a second wavelength for the second waveguide;
    a first tuning element positioned adjacent the first tunable grating and configured to independently alter the first tunable grating, thereby changing a resonance of the first tunable grating; and
    a second tuning element positioned adjacent the second tunable grating and configured to independently alter the second tunable grating, thereby changing a resonance of the second tunable grating,
    wherein the first tuning element and the second tuning element each comprise at least one of a mechanical tuning element, an optical tuning element, and an electrical tuning element.

2. The optical sensor of claim 1, the tuning element comprising a thermal component positioned adjacent the first tunable grating and configured to heat the first tunable grating, thereby changing a resonance of the first tunable grating.

3. The optical sensor of claim 1, the tuning element comprising a thin film resistor positioned adjacent the first tunable grating and configured to receive an electrical current and heat the first tunable grating, thereby changing a resonance of the first tunable grating.

4. The optical sensor of claim 1, wherein the first waveguide comprises a receiving facet shaped to receive an optical fiber such that radiation supplied by the optical fiber is transferred through the first waveguide to the first tunable grating.

5. The optical sensor of claim 1, wherein the channel comprises a chemical adhesion layer.

6. The optical sensor of claim 1, further comprising:
    a first thermal component positioned adjacent the first tunable grating and configured to heat the first tunable grating, thereby changing a resonance of the first tunable grating; and
    a second thermal component positioned adjacent the second tunable grating and configured to heat the second tunable grating, thereby changing a resonance of the second tunable grating,
    wherein the resonance of the first tunable grating differs from the resonance of the second tunable grating.

7. The optical sensor of claim 1, further comprising:
    a first thin film resistor positioned adjacent the first tunable grating and configured to receive a first electrical current and heat the first tunable grating, thereby changing a resonance of the first tunable grating; and
    a second thin film resistor positioned adjacent the second tunable grating and configured to receive a second electrical current and heat the second tunable grating, thereby changing a resonance of the second tunable grating,
    wherein the resonance of the first tunable grating differs from the resonance of the second tunable grating.

8. The optical sensor of claim 1, wherein the second waveguide is arranged on a side of the channel opposite the first waveguide and is configured to receive radiation guided through the fluid material by the first waveguide.

9. The optical sensor of claim 1, wherein the first waveguide and the second waveguide are arranged on a same side of the channel and the second waveguide is configured to guide radiation through the channel.

10. The optical sensor of claim 9, wherein the resonance of the first tunable grating differs from the resonance of the second tunable grating.

11. The optical sensor of claim 10, further comprising at least one sensor configured to simultaneously detect radiation guided through the channel by the first waveguide and the second waveguide, thereby facilitating parallel testing of the fluid material.

12. The optical sensor of claim 11, wherein the parallel testing of the fluid material comprises parallel testing using a plurality of optical analysis methods comprising at least one of a Raman scattering analysis, a white light spectroscopy analysis, and an absorption analysis.

13. An optical sensor assembly comprising:
a radiation source;
a sensor; and
at least one optical sensor positioned between the radiation source and the sensor, the at least one optical sensor comprising:
 a channel configured to transport a fluid material to be examined,
  a first waveguide positioned adjacent to the channel and configured to guide radiation through the channel,
  a first tunable grating defined on the first waveguide and configured to variably define a first cavity for selecting a first wavelength of the radiation for the first waveguide;
  a second waveguide positioned adjacent to the channel and configured to receive radiation passing through the fluid material;
  a second tunable grating defined on the second waveguide and configured to variably define a second cavity for selecting a second wavelength for the second waveguide;
  a first tuning element positioned adjacent the first tunable grating and configured to independently alter the first tunable grating, thereby changing a resonance of the first tunable grating,
  a second tuning element positioned adjacent the second tunable grating and configured to independently alter the second tunable grating, thereby changing a resonance of the second tunable grating,
  wherein the first tuning element and the second tuning element each comprise at least one of a mechanical tuning element, an optical tuning element, and an electrical tuning element.

14. The optical sensor assembly of claim 13, wherein the tuning element comprises a thermal component positioned adjacent the first tunable grating and configured to heat the first tunable grating, thereby changing a resonance of the first tunable grating.

15. The optical sensor assembly of claim 13, wherein the tuning element comprises a thin film resistor positioned adjacent to the first tunable grating and configured to receive an electrical current and heat the first tunable grating, thereby changing a resonance of the first tunable grating.

16. The optical sensor assembly of claim 13, wherein the first waveguide comprises a receiving facet shaped to receive an optical fiber such that radiation supplied by the optical fiber is transferred through the first waveguide to the first tunable grating.

17. The optical sensor assembly of claim 13, wherein the optical sensor further comprises:
a first thermal component positioned adjacent the first tunable grating and configured to heat the first tunable grating, thereby changing a resonance of the first tunable grating; and
a second thermal component positioned adjacent the second tunable grating and configured to heat the second tunable grating, thereby changing a resonance of the second tunable grating,
wherein the resonance of the first tunable grating differs from the resonance of the second tunable grating.

18. The optical sensor assembly of claim 13, wherein the optical sensor further comprises:
a first thin film resistor positioned adjacent the first tunable grating and configured to receive a first electrical current and heat the first tunable grating, thereby changing a resonance of the first tunable grating; and
a second thin film resistor positioned adjacent the second tunable grating and configured to receive a second electrical current and heat the second tunable grating, thereby changing a resonance of the second tunable grating,
wherein the resonance of the first tunable grating differs from the resonance of the second tunable grating.

19. An optical sensor comprising:
a first channel configured to transport a fluid material to be examined;
a first waveguide positioned adjacent to the first channel and configured to guide radiation through the first channel;
a first tunable grating defined on the first waveguide and configured to variably define a first cavity for selecting a first wavelength of the radiation; and
a reference channel positioned adjacent to the first channel and configured to transport a reference fluid;
a second waveguide positioned adjacent to the reference channel and configured to guide radiation through the reference channel; and
a second tunable grating defined on the second waveguide and configured to variably define a second cavity for selecting a second wavelength of the radiation.

20. The optical sensor of claim 19, further comprising a thermal component positioned adjacent the first tunable grating and configured to heat the first tunable grating, thereby changing a resonance of the first tunable grating.

21. The optical sensor of claim 19, further comprising a thin film resistor positioned adjacent the first tunable grating and configured to receive an electrical current and heat the first tunable grating, thereby changing a resonance of the first tunable grating.

22. A method of analyzing a fluid material, the method comprising:
providing:
 an optical sensor comprising a channel configured to transport a fluid material,
 a first waveguide positioned adjacent to the channel and configured to guide radiation through the channel,
 a first tunable grating defined on the first waveguide and configured to variably define a first cavity for selecting a first wavelength of the radiation for the first waveguide, a second waveguide positioned adjacent to the channel and configured to receive radiation passing through the fluid material, a second tunable grating defined on the second waveguide and configured to variably define a second cavity for selecting a second wavelength for the second waveguide, a first tuning element positioned adjacent the first tunable grating and configured to independently alter the first tunable grating, thereby changing a resonance of the first tunable grating, and a second tuning element positioned adjacent the second tunable grating and configured to independently alter the second tunable grating, thereby changing a resonance of the second tunable grating, wherein the first tuning element and the second tuning element each comprise at least one of a mechanical tuning element, an optical tuning element, and an electrical tuning element;

transporting the fluid material through the channel past the first waveguide and the second waveguide; and analyzing the fluid material based upon radiation passed through the fluid material.

23. The method of claim 22, further comprising:

providing a radiation source configured to direct radiation through the first waveguide; and providing a sensor configured to receive the radiation passed through the fluid material.

24. The method of claim 22, wherein analyzing the fluid material further comprises analyzing the fluid material based upon radiation passed through the fluid material from both the first waveguide and the second waveguide.

25. The method of claim 22, further comprising applying heat to the first tunable grating, thereby changing a resonance of the first tunable grating.

26. The method of claim 22, further comprising applying an electrical current to a thin film resistor positioned adjacent the first tunable grating, thereby heating the first tunable grating and changing a resonance of the first tunable grating.

* * * * *